US012788554B2

(12) United States Patent
Simonov et al.

(10) Patent No.: US 12,788,554 B2
(45) Date of Patent: Nov. 10, 2026

(54) OPHTHALMIC LENS

(71) Applicant: HOYA Medical Singapore Pte. Ltd., Singapore (SG)

(72) Inventors: Alexey Nikolaevich Simonov, Singapore (SG); Varinderpal Kaur, Singapore (SG)

(73) Assignee: HOYA Medical Singapore Pte. Ltd., Singapore (SG)

( * ) Notice: Subject to any disclaimer, the term of this patent is extended or adjusted under 35 U.S.C. 154(b) by 758 days.

(21) Appl. No.: 18/022,104

(22) PCT Filed: Aug. 18, 2021

(86) PCT No.: PCT/JP2021/031062
§ 371 (c)(1),
(2) Date: Feb. 17, 2023

(87) PCT Pub. No.: WO2022/039280
PCT Pub. Date: Feb. 24, 2022

(65) Prior Publication Data

US 2023/0320842 A1 Oct. 12, 2023

(30) Foreign Application Priority Data

Aug. 18, 2020 (EP) .................................... 20191603

(51) Int. Cl.
*A61F 2/16* (2006.01)
*G02C 7/02* (2006.01)

(52) U.S. Cl.
CPC .............. *A61F 2/164* (2015.04); *G02C 7/028* (2013.01)

(58) Field of Classification Search
None
See application file for complete search history.

(56) References Cited

U.S. PATENT DOCUMENTS

2004/0230299 A1 11/2004 Simpson et al.
2006/0244904 A1 * 11/2006 Hong ....................... G02C 7/02 351/159.01

(Continued)

FOREIGN PATENT DOCUMENTS

CN 1976649 A 6/2007
JP 2014503274 A 2/2014

(Continued)

OTHER PUBLICATIONS

International Preliminary Report on Patentability dated Feb. 16, 2023 for corresponding International Application No. PCT/JP2021/031062 filed Aug. 18, 2021; total pp. 10.

(Continued)

*Primary Examiner* — Javier G Blanco
(74) *Attorney, Agent, or Firm* — Snell & Wilmer (LA)

(57) ABSTRACT

The invention relates to an ophthalmic lens comprising a lens surface with a lens profile being representable by a combination of a standard aspheric profile and an even-order aspheric profile. The aspheric profiles are combined such that, in a region immediately surrounding the vertex of the lens surface, the lens profile converges to a sum of the standard aspheric profile and the even-order aspheric profile with decreasing radial distance to the vertex and, in an outer region surrounding the vertex, the lens profile converges to the standard aspheric profile with increasing radial distance to the vertex.

11 Claims, 20 Drawing Sheets

(56) References Cited

U.S. PATENT DOCUMENTS

| | | | | |
|---|---|---|---|---|
| 2010/0057202 | A1 | 3/2010 | Bogaert | |
| 2014/0104563 | A1 | 4/2014 | Bakaraju | |
| 2014/0309736 | A1 | 10/2014 | Sanger et al. | |
| 2017/0245983 | A1* | 8/2017 | Hong .................... | A61F 2/1616 |
| 2018/0325658 | A1* | 11/2018 | Canovas Vidal ..... | A61F 2/1654 |
| 2020/0004045 | A1 | 1/2020 | Shimojyou et al. | |
| 2020/0022806 | A1 | 1/2020 | Canovas Vidal et al. | |
| 2020/0330218 | A1 | 10/2020 | Canovas Vidal et al. | |

FOREIGN PATENT DOCUMENTS

| | | | |
|---|---|---|---|
| JP | 2015514233 | A | 5/2015 |
| JP | 2016501650 | A | 1/2016 |
| JP | 2016502430 | A | 1/2016 |

OTHER PUBLICATIONS

International Search Report dated Jan. 4, 2022, for corresponding International Application No. PCT/JP2021/031062 filed Aug. 18, 2021; total pp. 4.

Written Opinion of the International Searching Authority dated Jan. 4, 2022, for corresponding International Application No. PCT/JP2021/031062 filed Aug. 18, 2021; total pp. 9.

Office Action dated May 7, 2025, in corresponding European Patent Application No. 21777598 filed Aug. 18, 2021; total 7 pages.

* cited by examiner

OPHTHALMIC LENS

CROSS-REFERENCE TO RELATED APPLICATIONS

The present application is a U.S. National Stage entry under 35 U.S.C. § 371 of International Application No. PCT/JP2021/031062 filed Aug. 18, 2021, which claims priority to, and the benefit of European Application No. 20191603.8 filed Aug. 18, 2020, which applications are hereby incorporated by reference in their entirety.

FIELD OF THE INVENTION

The invention relates to an ophthalmic lens and to a manufacturing method for manufacturing the ophthalmic lens.

BACKGROUND OF THE INVENTION

It is known to use optical lenses with refractive lens profiles for ophthalmological purposes. Such refractive ophthalmic lenses are typically designed to provide for sharp vision at substantially one particular distance. Hence, the focal point of such lenses is typically quite localized, with a relatively narrow depth of focus, which can be understood as the distance on either side of the point of best focus through which vision is distinct. The narrow depth of focus leads to the problem that the visual acuity at other distances remains unsatisfactory. For instance, a cataract patient who had his natural crystalline lens removed during cataract surgery and replaced by an intraocular ophthalmic lens with a typical refractive surface profile will usually regain sharp vision at only one of far, intermediate and near distances, while he or she will still need to wear glasses for all other distances.

Intraocular lenses allowing for an extended depth of focus have recently become available, wherein various optical concepts have been explored, including diffractive multifocality, refractive multifocality and pinhole designs. While these approaches lead to improvements regarding the visual acuity at more than one distance, there remains the need for extending the depth of focus of an ophthalmic lens, particularly an intraocular lens, towards intermediate vision distances without compromising the visual performance at far vision distances.

SUMMARY OF THE INVENTION

It is an object of the present invention to provide an ophthalmic lens having good far vision performance and improved intermediate vision performance.

In a first aspect of the present invention, an ophthalmic lens comprising a lens surface with a lens profile being representable by a combination of a standard aspheric profile and an even-order aspheric profile is provided, wherein the aspheric profiles are combined such that, in a region immediately surrounding the vertex of the lens surface, the lens profile converges to a sum of the standard aspheric profile and the even-order aspheric profile with decreasing radial distance to the vertex and, in an outer region surrounding the vertex, the lens profile converges to the standard aspheric profile with increasing radial distance to the vertex.

It has been found that a lens surface profile which gives rise to an extended depth of focus towards intermediate vision distance can be presented by combining a standard aspheric profile with an even-order aspheric profile if the combination is such that, in a region immediately surrounding the vertex of the lens surface, the lens profile converges to a sum of the standard aspheric profile and the even-order aspheric profile with decreasing radial distance to the vertex and, in an outer region surrounding the vertex, the lens profile converges to the standard aspheric profile with increasing radial distance to the vertex. In particular, an ophthalmic lens having such a surface profile can lead to a focus which is extended towards higher optical powers and thereby provide for an improved visual acuity at intermediate distances without compromising the visual acuity at far distances. The proposed ophthalmic lens surface profile can also lead to a higher insensitivity with respect to decentrations of the lens.

The radial direction is perpendicular to a central axis of the ophthalmic lens, wherein the central axis may be an axis of symmetry, preferably rotational symmetry, of the lens surface. The vertex is the position where the central axis traverses the lens surface.

The aspheric profiles are non-spherical profiles. Hence, the aspheric profiles are preferably profiles having a curvature that is not the same everywhere in radial direction, giving rise to a non-constant distribution of optical powers across the lens surface. The standard aspheric profile preferably has the form of a conic section, particularly of a parabola. More specifically, the standard aspheric profile may correspond to a conic section as disclosed, for example, in the textbook "Modern Optical Engineering" by W. J. Smith (McGraw-Hill, 2000) or in the user manual of the ray-tracing software Zemax OpticStudio, version 19.4 (Zemax LLC, 2019).

The even-order aspheric profile is preferably given by a polynomial function of the radial distance having only even-order terms. Hence, for instance, the standard aspheric profile differs from the even-order aspheric profile in that the standard aspheric profile cannot be accurately described by a polynomial function, in particular, not even by a rational function.

The combination of the aspheric profiles refers to a combination applying preferentially to the whole lens profile. This is to say, if the lens profile is represented by a combination of the standard aspheric profile and the even-order aspheric profile, for instance, the sag of every point of the lens profile can be represented as a combination of a corresponding point sag of the standard aspheric profile and a corresponding point sag of the even-order aspheric profile. In an embodiment, the lens profile can be represented by a function of the radial distance to the vertex, wherein the function depends on a first aspheric function describing the standard aspheric profile and a second aspheric function describing the even-order aspheric profile, such that the value of the function describing the lens profile at any radial distance is given by a linear combination of the value of the first aspheric function and the value of the second aspheric function at that radial distance. The function representing the lens profile can be a sag function, for instance.

Preferably, therefore, the lens profile of the lens surface of the ophthalmic lens can be understood as defining a single refractive zone, wherein the refractive power varies across the zone.

The convergence of the lens profile to a sum of the standard aspheric profile and the even-order aspheric profile with decreasing radial distance to the vertex is preferably a convergence in an inner region surrounding the vertex, particularly in a neighborhood of the vertex. Hence, the lens profile may be viewed as varying between being approximately described by a sum of the standard aspheric profile and the even-order aspheric profile in the inner region surrounding the vertex, particularly the neighborhood of the vertex, towards being approximately described by the standard aspheric profile in the outer region surrounding the vertex. The outer region surrounding the vertex is preferably a neighborhood of an outer boundary of the lens surface. The convergence of the lens profile can be tested for a given function of the radial distance representing the lens profile by, for instance, expanding the function in a power series in the radial distance at a) the vertex and b) the outer boundary of the lens surface and comparing the terms in the power series to corresponding terms in a power series of a standard aspheric profile function, particularly at least the first two non-constant terms. Alternatively, the given function may be expressed in terms of a standard aspheric profile function and a remaining part, wherein the limits of the remaining part may be determined for a) the vertex and b) the outer boundary of the lens surface.

In an embodiment, the combination of the standard aspheric profile and the even-order aspheric profile is representable by a smooth function of the radial position, i.e. of the radial distance to the vertex. This can lead to reduced optical aberrations, which may cause photic phenomena. A smooth function is understood herein as a function whose second derivative does not comprise any kinks, or, whose third derivative is continuous. In particular, the smooth function may be understood as a function whose derivatives are all continuous, i.e., which is infinitely differentiable.

In an embodiment, the combination of the standard aspheric profile and the even-order aspheric profile is representable by a function of the radial position, which has a first order derivative of zero at the vertex of the lens surface. This can avoid negative optical effects that will arise from a kink at the vertex.

In an embodiment, the combination of the standard aspheric profile and the even-order aspheric profile is representable by a function of the radial position, which changes the sign of the second-order derivative with increasing radial position. The ophthalmic lens can in this way be particularly insensitive against decentrations, i.e. deviations of its central axis from the optical axis. Also, an insensitivity against a tilt of the lens with respect to the optical axis can be achieved in this way. The insensitivity against decentrations and tilts refers to an insensitivity of optical properties of the lens, such as, for instance, a focal position and a depth of focus of the lens. The optical properties may be measured in terms of a modulation transfer function, particularly a through focus modular transfer function.

Since the optical power associated with the lens profile is related to the second-order derivative of the function representing the phase of a light wave propagating through the lens, assuming that the index of refraction of the lens material is constant, the phase is defined solely by the surface profile of the lens. One may conclude that the change in sign of the second-order derivative of the surface profile with increasing radial position leads to a corresponding change in the optical power along the radial position, i.e. with increasing radial distance to the vertex.

Preferably, the second-order derivative of the function representing the lens profile changes its sign with increasing radial position such that the optical power associated with the lens profile changes from a positive value to a negative value and then back to a positive value with increasing radial position. Furthermore, it is possible that the sign of the second-order derivative of the function representing the lens profile changes with increasing radial position such that the optical power associated with the lens profile changes sign an uneven number of times, the number being, for instance, 3 or 5. The optical power associated with the lens profile may, in particular, be measured relative to its value at the vertex.

It is preferred that the second-order derivative of the function representing the lens profile changes its sign only in an inner region of the lens surface extending from the vertex to a radial distance to the vertex of less than or equal to two-thirds of the overall radial extent of the lens surface, preferably less than or equal to half of the overall radial extent of the lens surface. If the lens is an intraocular lens, the overall radial extent of the lens surface may reach approximately 3 mm, for instance.

In a preferred embodiment, the sag function of the standard aspheric profile is defined by $$S_1(r) = \frac{cr^2}{1 + \sqrt{1 - (1 + k)c^2r^2}}, \tag{1}$$

wherein r denotes the radial distance to the vertex of the lens surface, c denotes the curvature at the vertex of the lens surface and k denotes the conic constant. The conic constant k is preferably negative. The curvature c at the vertex of the lens surface is preferably positive. In an embodiment, the curvature c at the vertex of the lens surface is a) larger than or equal to 0.005 $mm^{-1}$ and b) smaller than or equal to 0.25 $mm^{-1}$. In a preferred embodiment, the curvature c at the vertex of the lens surface is a) larger than or equal to 0.005 $mm^{-1}$ and b) smaller than or equal to 0.08 $mm^{-1}$. Moreover, the conic constant k is preferably a) larger than or equal to −800 and b) smaller than or equal to 5. In a preferred embodiment, the conic constant k is a) larger than or equal to −800 and b) smaller than or equal to −5. It has been found that using such a standard aspheric profile allows for a further improved optical performance of the ophthalmic lens.

In the present document, a sag function representing a lens profile is understood as a measure of a depth of the lens profile with respect to a constant height given by the axial position of the vertex of the lens surface comprising the lens profile. The same lens profile could, for instance, also be represented by a function measuring the height of the lens surface with respect to a plane virtually intersecting the lens orthogonal to the central axis of the lens and/or the optical axis, wherein this alternative function may be given, for instance, by the difference between a constant and the sag function of the lens profile.

In an embodiment, the sag function of the even-order aspheric profile is defined by $$S_2(r) = \sum_{n=1}^{8} A_{2n} r^{2n}, \tag{2}$$

wherein r denotes the radial distance to the vertex of the ophthalmic lens surface and the $A_{2n}$ are constants. Preferably, the change in sign of the second-order derivative of the function representing the lens profile with increasing radial position corresponds to one or more ratios between the constants $A_{2n}$. The values of the constants $A_{2n}$ preferably range from values at the order of $-10^{-2}$ to values at the order of $10^{-2}$ when given in units of $mm^{-2n+1}$, respectively. It has been found that using such an even-order aspheric profile also allows for a further improved optical performance of the ophthalmic lens.

In a preferred embodiment, the combination of the standard aspheric profile and the even-order aspheric profile is defined by a combination function, which depends on the radial distance to the vertex such that the contribution of the standard aspheric profile and the contribution of the even-order aspheric profile to the lens profile at a certain radial distance to the vertex depends on the radial distance. Hence, for instance, the sag function of the standard aspheric profile and the sag function of the even-order aspheric profile are not simply proportional to each other, such that the function representing the lens profile is not simply a linear combination of the two sag functions.

In an embodiment, the sag function of the lens profile is defined by $$S(r)=M(r)S_1(r)+(1-M(r))(S_1(r)+S_2(r)), \qquad (3)$$

wherein r denotes the radial distance to the vertex of the lens surface, $S_1(r)$ denotes a sag function of the standard aspheric profile, $S_2$ (r) denotes a sag function of the even-order aspheric profile and M(r) denotes the combination function. In particular, $S_1(r)$ and $S_2(r)$ may denote the sag functions given in above equations (1) and (2). The above equation (3) can equivalently be expressed as $$S(r)=S_1(r)+(1-M(r))S_2(r). \qquad (4)$$

The combination function preferably tends to 0 towards the vertex of the lens surface and preferably tends to 1 towards an outer boundary of the lens surface. It is also preferred that the combination function M(r) monotonically increases in the radial direction, i.e. decreases nowhere in the radial direction. It has been found that using such a combination function also allows for a further improved optical performance of the ophthalmic lens.

In an embodiment, the combination function is a smooth function. Preferably, the combination function is defined by $$M(r)=\tfrac{1}{2}(1+\tan h(A(r-\rho))), \qquad (5)$$

wherein A and ρ are constants. More generally, it is preferred that the combination function increases in an intermediate radial region more rapidly than in an inner and an outer radial region. In an embodiment, the constant A is larger than 2.0 $mm^{-1}$ and smaller than 10.0 $mm^{-1}$, and the constant ρ is larger than 0.3 mm and smaller than 2.5 mm. In a preferred embodiment, the constant A is larger than 4.0 $mm^{-1}$ and smaller than 7.0 $mm^{-1}$, and the constant ρ is larger than 0.3 mm and smaller than 2.0 mm. Also these parameters lead to a further improved optical performance of the ophthalmic lens.

Preferentially, the sag function S(r) of the lens profile is determined by the following set of parameter ranges: $-800 \le k \le 5$; $0.005\ mm^{-1} \le c \le 0.25\ mm^{-1}$; $2.0\ mm^{-1} < A < 10.0\ mm^{-1}$; $0.3\ mm < \rho < 2.5\ mm$; $-1.5\times10^{-2}\ mm^{-1} < A_2 < 1.5\times10^{-2}\ mm^{-1}$, $-1.5\times10^{-2}\ mm^{-3} < A_4 < 1.5\times10^{-2}\ mm^{-3}$, $-9.0\times10^{-3}\ mm^{-5} < A_6 < 9.0\times10^{-3}\ mm^{-5}$; $-2.9\times10^{-2}\ mm^{-7} < A_8 < 2.9\times10^{-2}\ mm^{-7}$; $-3.0\times10^{-2}\ mm^{-9} < A_{10} < 3.0\times10^{-2}\ mm^{-9}$; $-1.2\times10^{-4}\ mm^{-11} < A_{12} < 1.2\times10^{-4}\ mm^{-11}$; $-1.2\times10^{-4}\ mm^{-11} < A_{14} < 1.2\times10^{-4}\ mm^{-11}$, $-1.2\times10^{-4}\ mm^{-11} < A_{16} < 1.2\times10^{-4}\ mm^{-11}$. In a particular embodiment, the sag function S(r) of the lens profile is determined by the following set of parameter ranges: $-800 \le k \le -5$; $0.005\ mm^{-1} \le c \le 0.08\ mm^{-1}$; $4.0\ mm^{-1} < A < 7.0\ mm^{-1}$; $0.3\ mm < \rho < 2.0\ mm$; $8.9\times10^{-5}\ mm^{-1} < A_2 < 3.0\times10^{-4}\ mm^{-1}$; $8.9\times10^{-3}\ mm^{-3} < A_4 < 1.2\times10^{-4}\ mm^{-3}$; $-9.0\times10^{-3}\ mm^{-5} < A_6 < -4.0\times10^{-3}\ mm^{-5}$; $-2.9\times10^{-2}\ mm^{-7} < A_8 < -2.0\times10^{-2}\ mm^{-7}$; $2.0\times10^{-2}\ mm^{-9} < A_{10} < 2.8\times10^{-2}\ mm^{-9}$; $-1.0\times10^{-4}\ mm^{-11} < A_{12} < 1.2\times10^{-4}\ mm^{-11}$; $A_{14}=0$; $A_{16}=0$.

In a preferred embodiment, the lens surface with the lens profile is a refractive lens surface. Hence, the lens surface with the lens profile preferably does not comprise any diffractive elements. In this way, the monofocality of the ophthalmic lens can be increased.

In a preferred embodiment, the ophthalmic lens is an intraocular lens. As an intraocular lens, the ophthalmic lens is intended to be placed into the capsular bag of a patient's eye after extracapsular cataract removal so as to function as a refractive medium replacing the natural crystalline lens of the eye. However, the ophthalmic lens may also be another kind of ocular lens, such as a contact lens or even a lens of glasses, i.e. eyeglasses.

In a further aspect of the present invention, a method for manufacturing an ophthalmic lens is presented, wherein the manufacturing method comprises forming a lens profile of a lens surface of the ophthalmic lens such that it is representable by a combination of a standard aspheric profile and an even-order aspheric profile, wherein the aspheric profiles are combined such that, in a region immediately surrounding the vertex of the lens surface, the lens profile converges to a sum of the standard aspheric profile and the even-order aspheric profile with decreasing radial distance to the vertex and, in an outer region surrounding the vertex, the lens profile converges to the standard aspheric profile with increasing radial distance to the vertex.

The lens profile might be formed, for instance, by using a known molding procedure or by another technique generally used for manufacturing lenses. In particular, the lens profile might be formed by cast molding.

In another aspect of the present invention, an ophthalmic lens is presented, which is producible by the manufacturing method.

It shall be understood that the ophthalmic lens of claim 1 and the manufacturing method of claim 9 have similar and/or identically preferred embodiments as defined in the dependent claims.

It shall be understood that a preferred embodiment of the invention can also be any combination of the dependent claims with the respective independent claim.

DETAILED DESCRIPTION OF EMBODIMENTS

Figure 1:
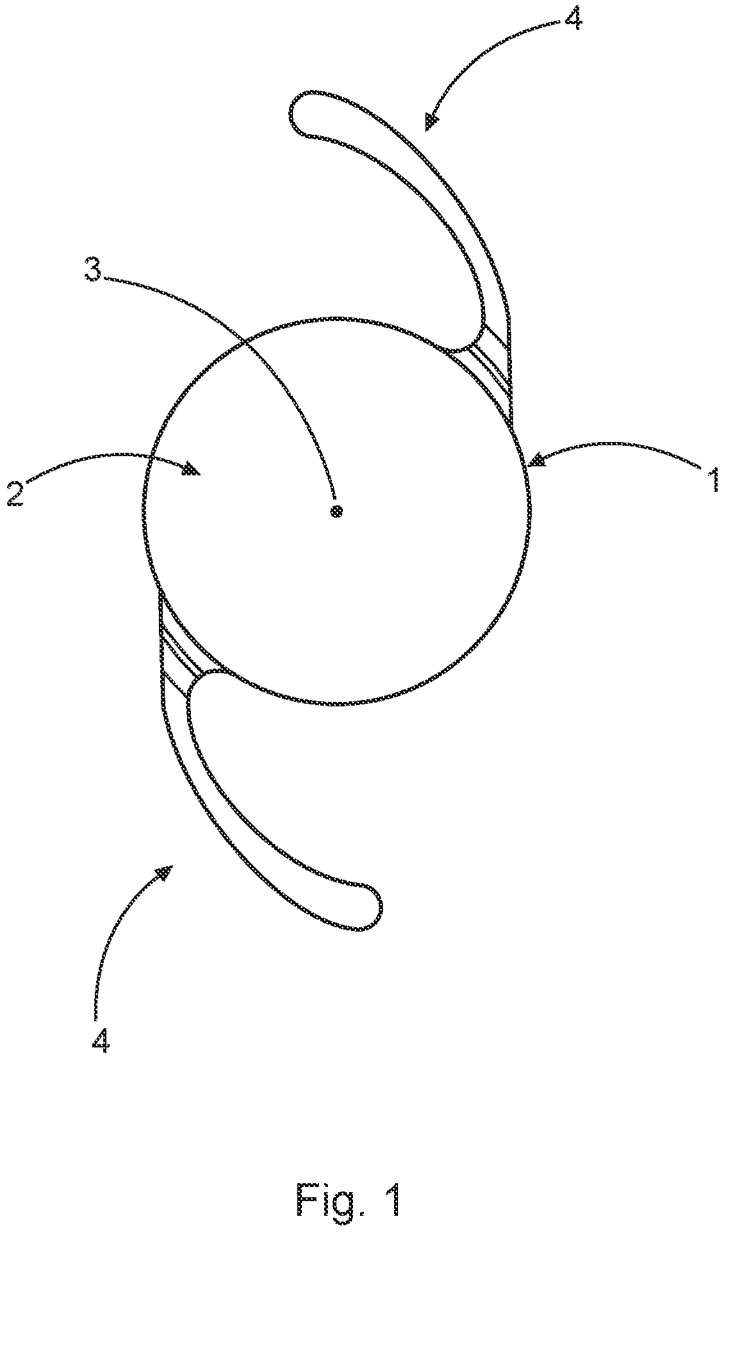
FIG. 1 shows schematically and exemplarily an embodiment of an ophthalmic lens.

FIG. 1 shows schematically and exemplarily an embodiment of an ophthalmic lens 1 having a smooth lens surface 2. The lens surface 2 is, in this embodiment, radially symmetric, i.e. symmetric against rotations about a central axis. The central axis virtually pierces through the lens surface 2 at a center 3 of the lens surface 2, wherein the center 3 is schematically indicated in FIG. 1 by a point. The lens 1 is attached to fixing elements 4 for fixing the lens 1 in an eye, in order to replace a natural lens, which has been removed, by the lens 1. Thus, the lens 1 is an intraocular lens.

Since the lens surface 2 is radially symmetric, the vertex of the lens surface 2 lies at the center 3. The curvature of the lens surface 2 of the lens 1 can be characterized by a lens profile, which corresponds to the line of intersection of the lens surface 2 with a virtual plane that includes the center of the lens surface 2 and is orthogonal to the plan view of FIG. 1. Since the lens surface 2 shown in FIG. 1 is radially symmetric, the so obtained lens profile is independent of the angular orientation of this virtual plane. In other embodiments, the lens surface 2 may comprise different lens profiles in different radial directions.

The lens surface 2 is an anterior surface of the lens 1 with a diameter, measured perpendicular to the central axis, i.e. in radial direction, of 6 mm. However, in other embodiments the diameter can also be smaller or larger. The anterior surface 2 is curved aspherically, i.e. is an aspheric surface. The lens 1 also has a posterior surface not shown in FIG. 1, which opposes the anterior surface 2. The posterior surface of the lens 1 can also be an aspheric surface, or it can be a spherical surface.

Due to their curvatures, the lens surfaces are refractive surfaces, wherein the two refractive surfaces jointly endow the ophthalmic lens 1 with an optical power. The material of the lens 1 is a hydrophobic acrylic material comprising an agent like benzotriazole for absorbing ultraviolet light and a blue-light filtering chromophore like monomethine, wherein the material is biocompatible and foldable. For more details regarding preferred lens materials, reference is made to U.S. Pat. Nos. 8,647,383 B2 and 9,265,603 B2. The refractive index of the lens material might be, for instance, 1.544.

Figure 2:
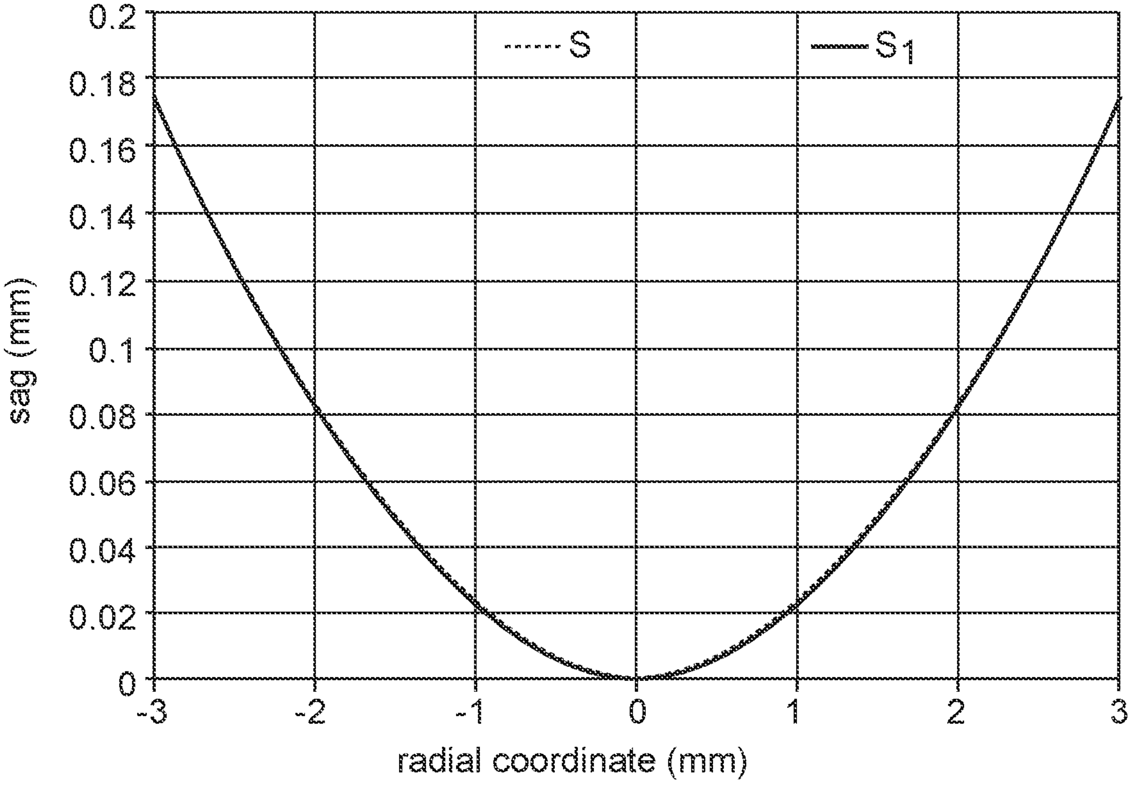
FIG. 2 shows schematically and exemplarily a sag function of the lens profile and a sag function of a standard aspheric profile.
Figure 3:
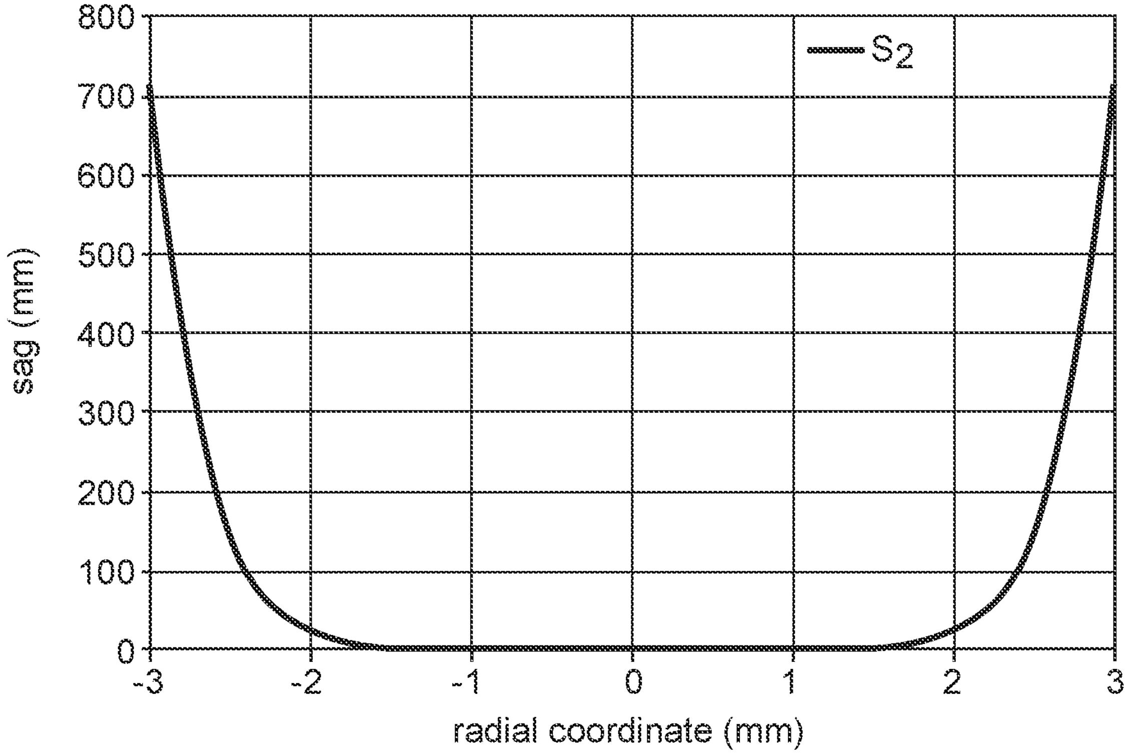
FIG. 3 shows schematically and exemplarily a sag function of an even-order aspheric profile.

FIG. 2 shows schematically and exemplarily a graph of the sag function S(r) representing the lens profile of the lens surface 2. FIG. 2 further shows schematically and exemplarily a graph of the sag function $S_1(r)$ of a standard aspheric profile, and FIG. 3 shows schematically and exemplarily a graph of the sag function $S_2(r)$ of an even-order aspheric profile, wherein the lens profile whose sag function S(r) is shown in FIG. 2 may be represented by a combination of the standard aspheric profile whose sag function $S_1(r)$ is shown in FIG. 2 and the even-order aspheric profile whose sag function $S_2(r)$ is shown in FIG. 3. The combination of the two aspheric profiles, which corresponds to a combination of the respective sag functions $S_1(r)$ and $S_2(r)$, can be represented by a combination function M(r). The horizontal axes of the graphs shown in FIGS. 2 and 3 indicate a radial coordinate, i.e. a coordinate defining the radial distance r of the respective position on the lens surface 2 to the vertex, as measured perpendicularly to the central axis of the lens 1.

As can be seen in FIG. 2, the lens surface sag function S(r) is a smooth function of the radial position r, meaning that particularly the first derivative of S(r) is continuous in the whole range of radial positions. The function S(r) takes positive values ranging from 0 at the lens center r=0 to about 0.175 mm at an outer boundary of the lens surface at a radius $r_B$=3 mm. At the vertex, which is located at the lens center r=0, the lens surface sag function S(r) has a vanishing first order derivative. In fact, in FIG. 2, the difference between the lens surface sag function S(r) and the standard aspheric profile sag function $S_1(r)$ is hardly visible due to the resolution of the axes of the illustrated graph. The standard aspheric profile sag function $S_1(r)$ is defined by above equation (1), wherein the curvature c at the vertex of the lens surface corresponds to a convex shape and the conic constant k is negative, which means that the shown standard aspheric profile is parabolic.

The value of c may be regarded as a reference curvature corresponding to a reference optical power of the lens 1, wherein the reference optical power might be selected based on a prescription in a clinical context.

The standard aspheric profile may also be regarded as a standard monofocal profile, because the lens having a surface with such a standard aspheric profile would give rise to essentially a single, substantially localized focal point. The reference optical power of the lens 1 whose sag function S(r) is shown in FIG. 2 is approximately 20 diopter, and the conic constant k is chosen appropriately. The reference optical power corresponds to the value c of the curvature at the vertex of the lens surface 2.

The even-order aspheric profile sag function $S_2(r)$ shown in the graph of FIG. 3 is defined by above equation (2), wherein the horizontal axis of the shown graph indicates the radial coordinate whose absolute value corresponds to the radial distance r to the vertex of the lens surface 2, and the constants $A_{2n}$ are appropriately chosen. Due to the very different resolution of the vertical axis of the graph illustrated in FIG. 3 as compared to the graph illustrated in FIG. 2, it appears as if the even-order aspheric profile sag function $S_2(r)$ is substantially 0 over half the radial extent of the lens surface 2. However, already in this inner region of the lens surface 2, the even-order aspheric profile is not negligible with respect to the standard aspheric profile whose sag function $S_1(r)$ is shown in FIG. 2.

Figure 4:
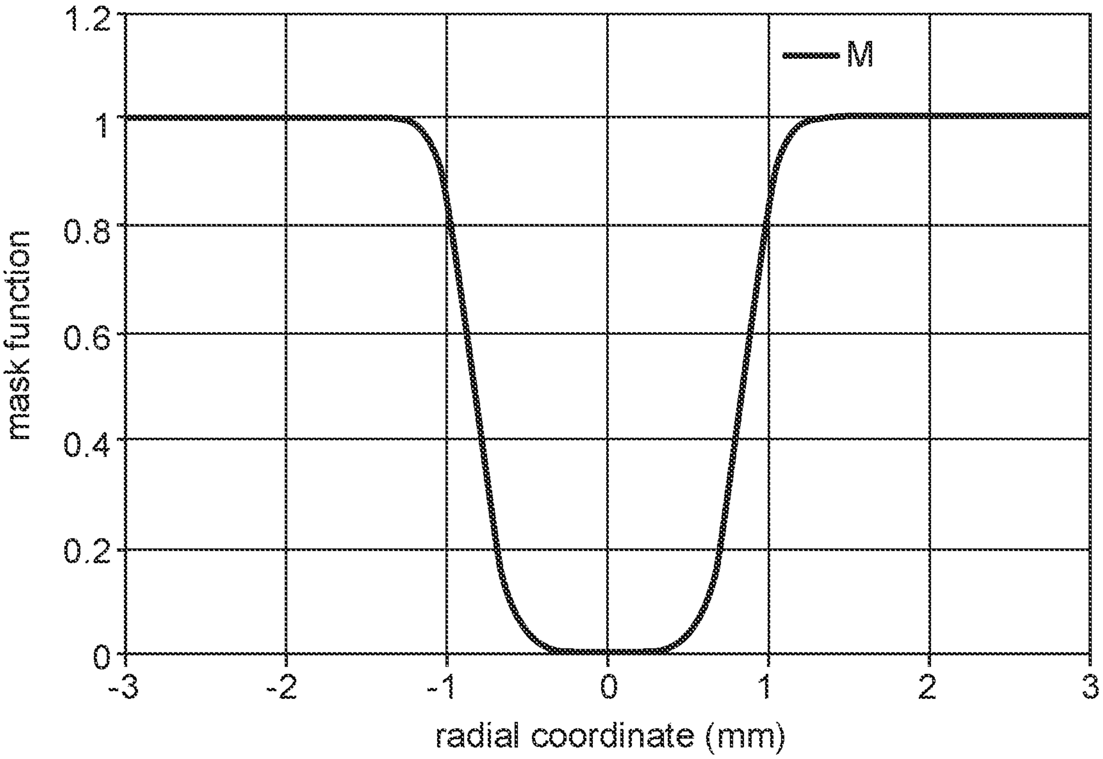
FIG. 4 shows schematically and exemplarily a combination function.

The combination function M(r) corresponding to the exemplary lens 1 is shown in FIG. 4. It is defined by a smooth function of the radial position r, and is of the form given in above equation (5), wherein the constants A and p are appropriately chosen. The lens surface sag function for the lens surface 2 shown in FIG. 2 is a combination of the standard aspheric profile sag function $S_1(r)$ shown in FIG. 2 and the even-order aspheric profile sag function $S_2(r)$ shown in FIG. 3, wherein the combination of the two sag functions is defined by the combination function M(r) shown in FIG. 4. In this embodiment, the combination function M(r) depends on the radial distance to the vertex such that the contribution of the standard aspheric profile sag function $S_1(r)$ and the contribution of the even-order aspheric profile sag function $S_2(r)$ to the lens profile sag function S(r) of the lens 1 at a certain radial distance to the vertex depends on the radial distance r. The combination function M(r) may therefore also be regarded as a mask function masking the contributions from the two different aspheric profiles, wherein the degree of masking depends on the radial position r.

The lens surface 2 described by the resulting lens profile sag function S(r) is shaped such that, in a region immediately surrounding the vertex of the lens surface 2, the lens profile converges to the sum of the standard aspheric profile, described by $S_1$ (r), and the even-order aspheric profile, described by $S_2$ (r), with decreasing radial distance r to the vertex and, in an outer region surrounding the vertex, the lens profile converges to the standard aspheric profile with increasing radial distance r to the vertex.

Since the standard aspheric profile sag function $S_1(r)$, the even-order aspheric profile sag function $S_2(r)$ and the combination function M(r) are all smooth functions in this embodiment, also the combined sag function, i.e. the lens profile sag function S(r), is smooth.

The aspheric profile sag functions $S_1(r)$ and $S_2(r)$ resulting in the lens profile sag function S(r) by combination are, in this embodiment, designed such that the second-order derivative of the lens profile sag function S(r) changes its sign with increasing radial position, which is reflected by an intermediate radial region in which the optical power associated with the lens surface 2 becomes negative. This region is an annular region of the lens surface 2 extending around a radial position of approximately 0.7 mm. The lens profile sag function S(r) of the lens 1 is defined by above equation (3), which is equivalent to above equation (4).

Figure 5:
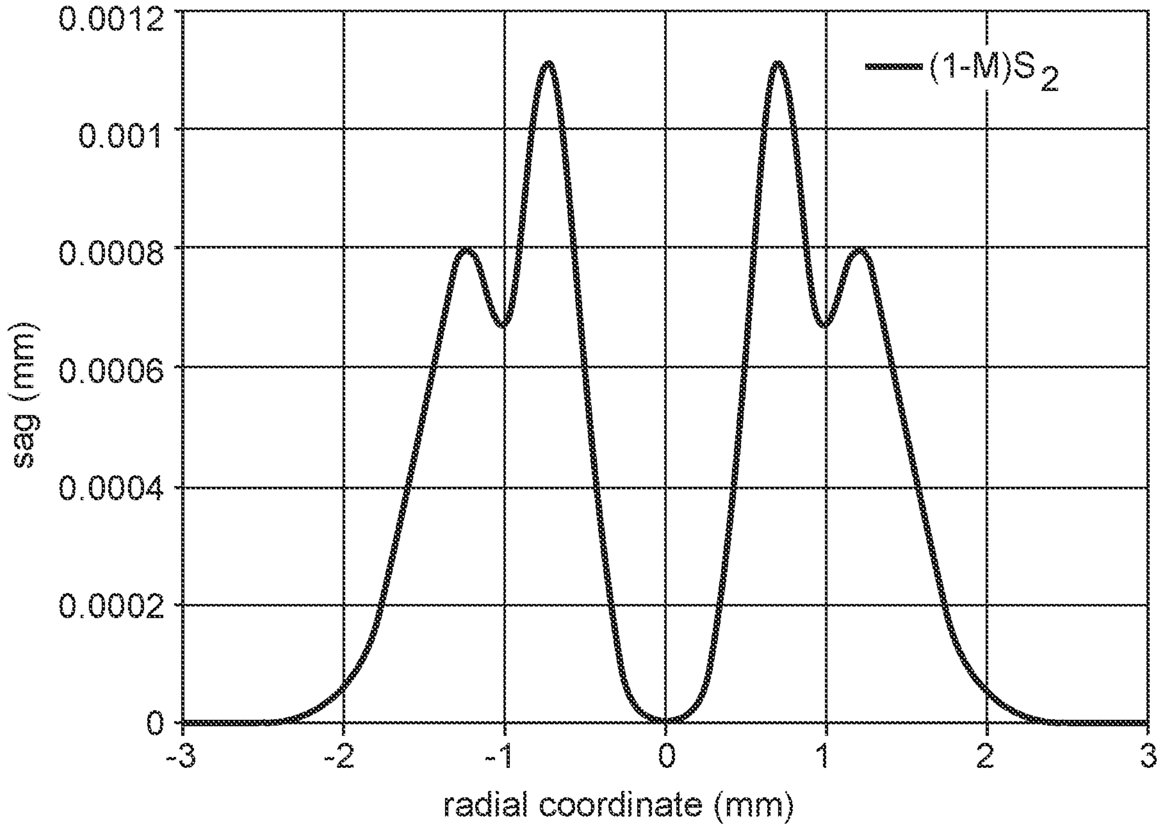
FIG. 5 shows schematically and exemplarily the difference between a sag function of a lens profile and a sag function of a standard aspheric profile.

The second term of equation (4), which corresponds to the difference $(1-M(r))\ S_2(r)$ between the lens profile sag function S(r) and the standard aspheric profile sag function $S_1(r)$, is shown in FIG. 5 for the embodiment also illustrated in FIGS. 1 to 4. From the values of this difference function $(1-M(r))\ S_2(r)$ as seen on the vertical axis of the graph illustrated in FIG. 5, it is apparent why the difference between the lens profile sag function S(r) and the standard aspheric profile sag function $S_1(r)$ is hardly visible in FIG. 2.

As will be illustrated in the following, while the values assumed by the difference function $(1-M(r))\ S_2(r)$ shown in FIG. 5 seem to be small, corresponding to only a seemingly small deviation of the lens surface 2 from a standard aspheric surface, the optical effects generated by the seemingly small deviation are surprisingly large. In fact, the deviation of the lens surface 2 from the standard aspheric surface may be designed to be just large enough and positioned just right such that the depth of focus of the lens 1 can be widened towards smaller focal distances. Moreover, the deviation can be designed to be still small enough and positioned just right such that undesired photic phenomena generated by the lens surface 2 can be avoided.

Figure 6:
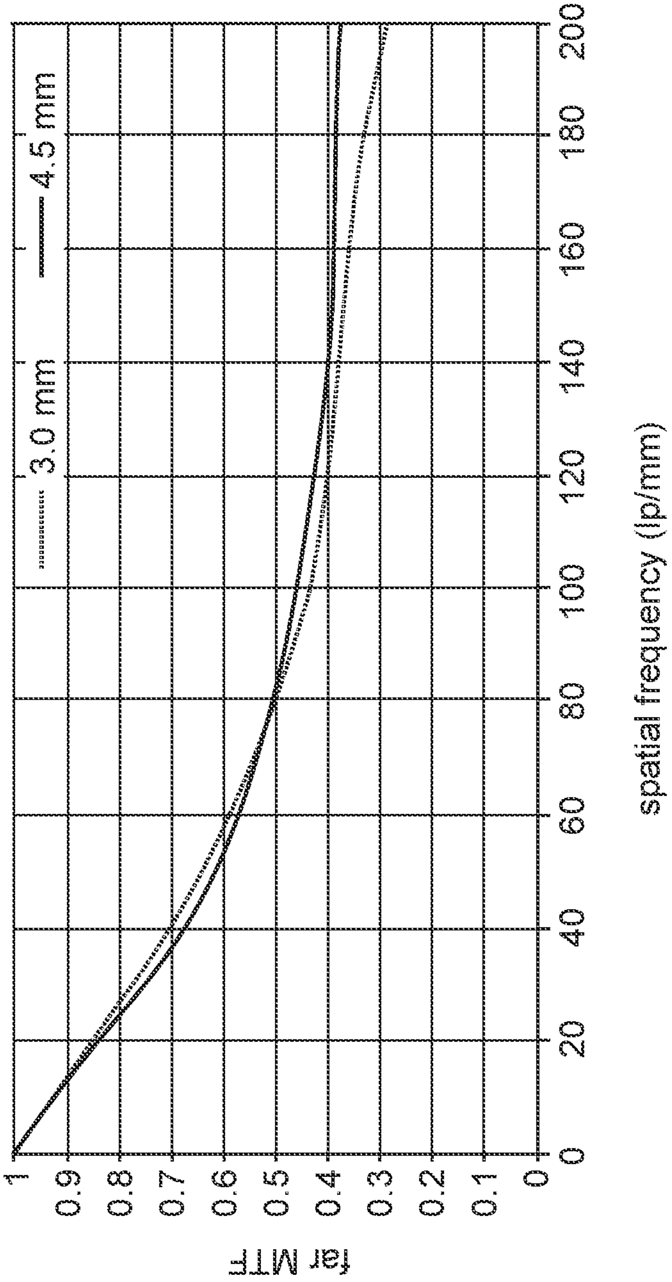
FIG. 6 shows schematically and exemplarily a far modulation transfer function.

FIG. 6 shows schematically and exemplarily a modulation transfer function (MTF) calculated for a human eye into which the ophthalmic lens 1 has been placed, with an aperture of 3.0 mm and 4.5 mm, respectively, wherein the calculation was performed for far visual distances. It can be seen in FIG. 6 that the modulation transfer function, which may be regarded as a measure of imaging quality, falls off only relatively slowly towards higher spatial frequencies irrespective of the aperture.

Figure 7:
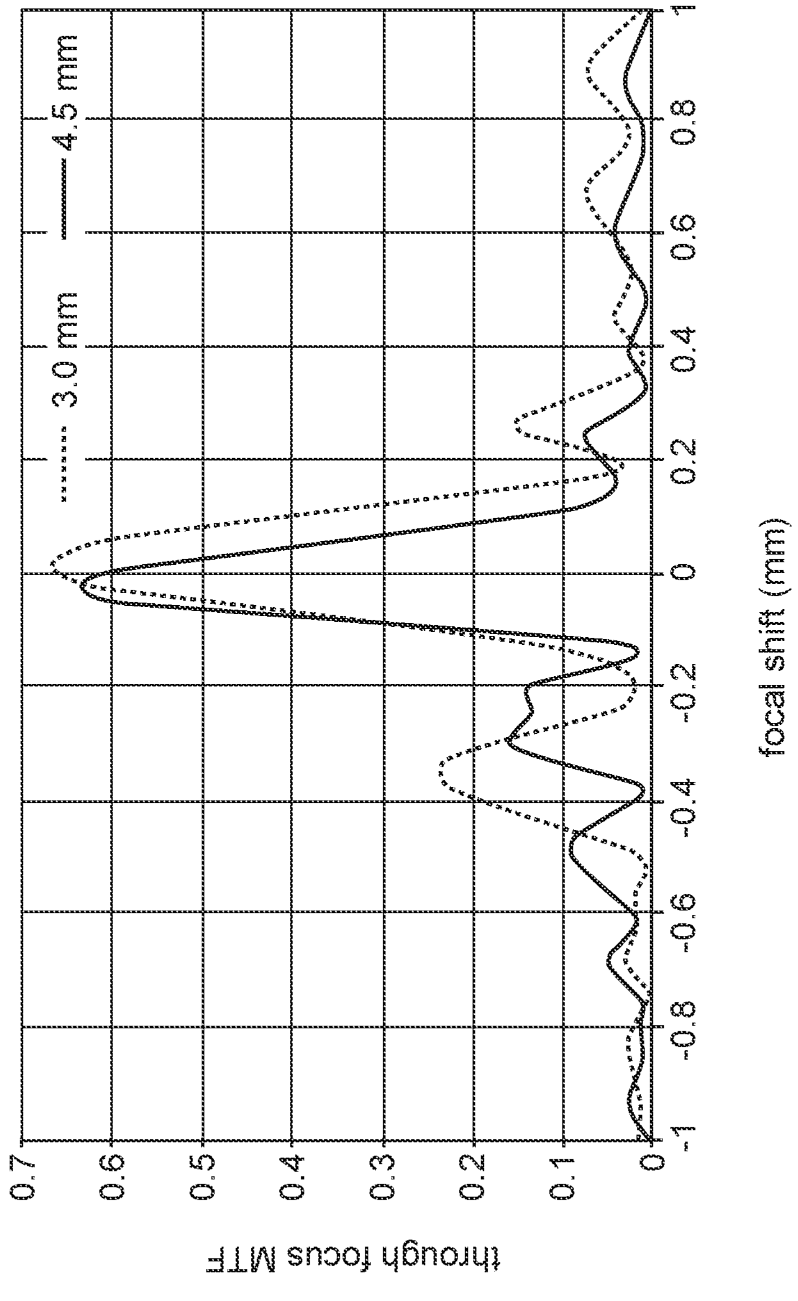
FIG. 7 shows schematically and exemplarily a through-focus modulation transfer function.

FIG. 7 shows schematically and exemplarily a through-focus modulation transfer function calculated for a human eye into which the lens 1 has been placed, at a spatial frequency of 50 line pairs per millimeter. A through-focus modulation transfer function may also be referred to as a through-focus response curve. In FIG. 7, the through-focus modulation transfer function is shown for an aperture of 3.0 mm and for an aperture of 4.5 mm. The horizontal axis indicates a focal shift, i.e. a focal distance measured relative to the focal distance corresponding to the reference optical power of the lens 1, wherein negative focal shifts correspond to higher optical powers with respect to the reference optical power. For both aperture sizes shown in FIG. 7, the width of the main, far-focus peak is widened with respect to a corresponding standard aspheric lens, particularly in the negative focal shift direction. Thus, FIG. 7 illustrates that the visual acuity of the human eye can be improved at intermediate vision distances.

Figure 8:
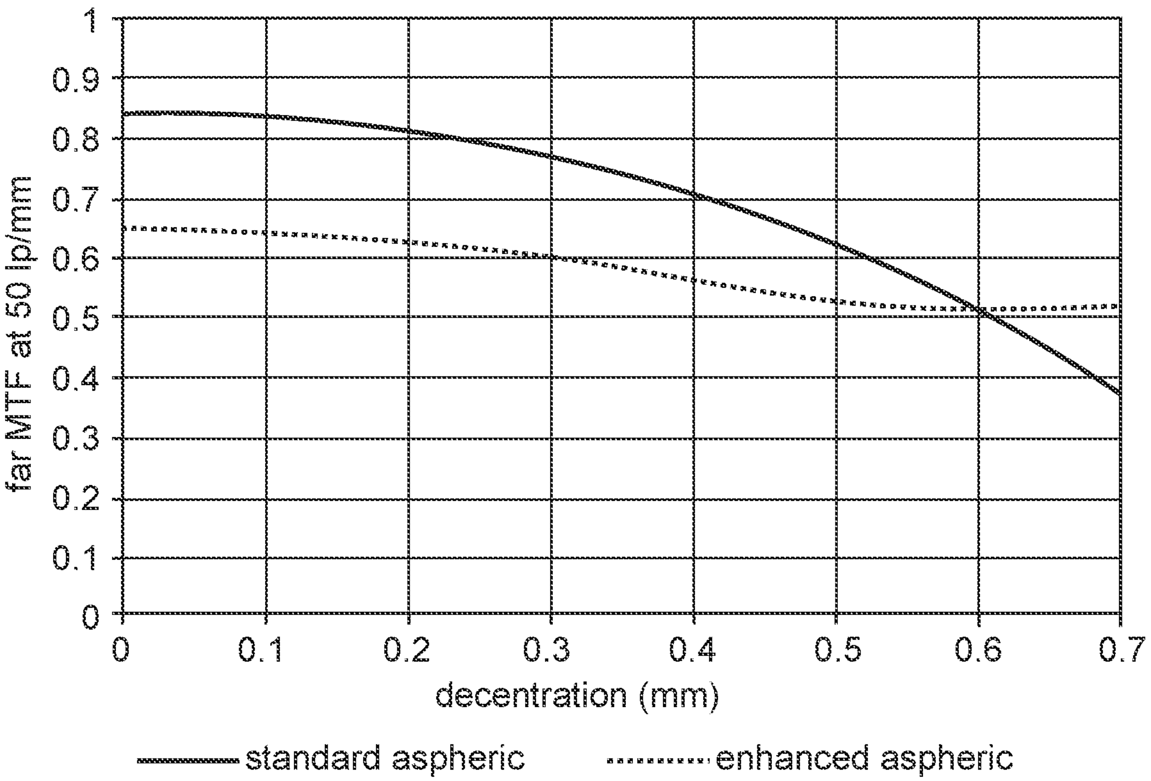
FIG. 8 shows schematically and exemplarily a far modulation transfer function at a particular spatial frequency depending on a lens decentration.
Figure 9:
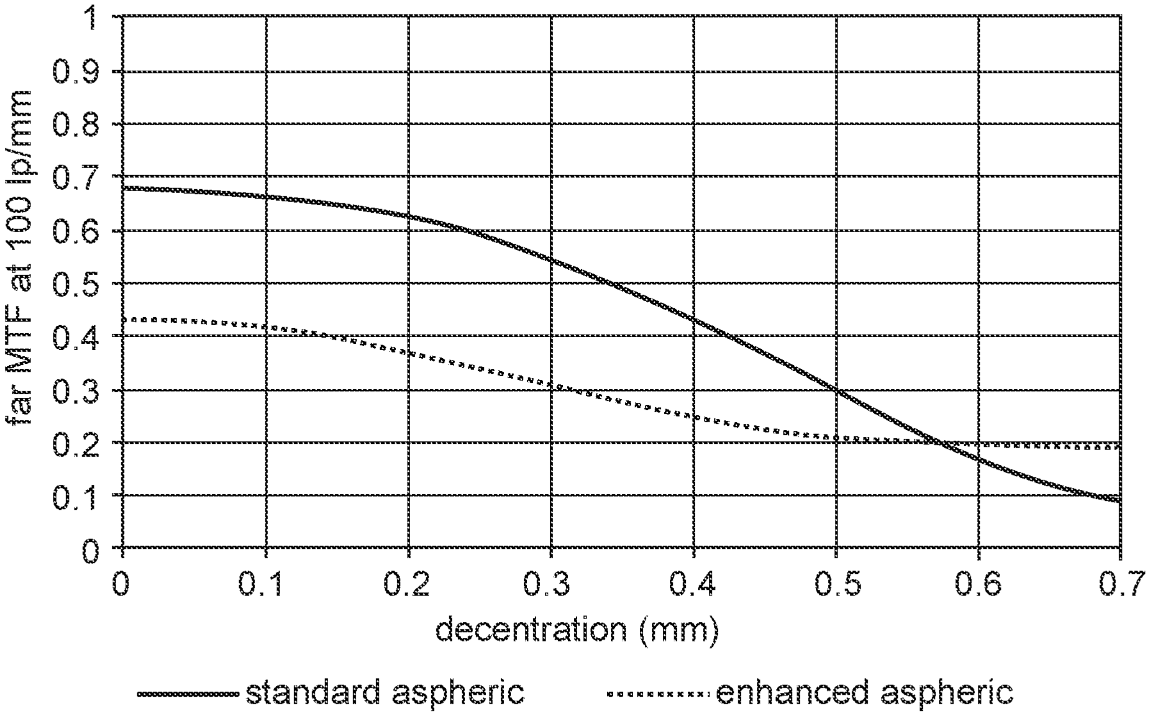
FIG. 9 shows schematically and exemplarily a far modulation transfer function at another particular spatial frequency depending on a lens decentration.

FIG. 8 schematically and exemplarily shows the modulation transfer function corresponding to the lens 1, which may be regarded as an enhanced aspheric lens, at a spatial resolution of 50 line pairs per millimeter, calculated for far vision distances and with an aperture of 3 mm, as compared to the one of a standard aspheric lens, in its dependence on the decentration of the lens, i.e. the deviation of the central axis of the lens surface from the optical axis. It can be seen in FIG. 8 that the value of the modulation transfer function decreases only relatively little as compared to the one corresponding to the standard aspheric lens. This behavior is also visible in FIG. 9, which corresponds to FIG. 8, except that the spatial resolution is chosen to be 100 line pairs per millimeter. For decentrations above approximately 0.6 mm, the modulation transfer function at both 50 line pairs per millimeter and 100 line pairs per millimeter is even higher for the lens 1 as compared to the standard aspheric lens.

Figure 10:
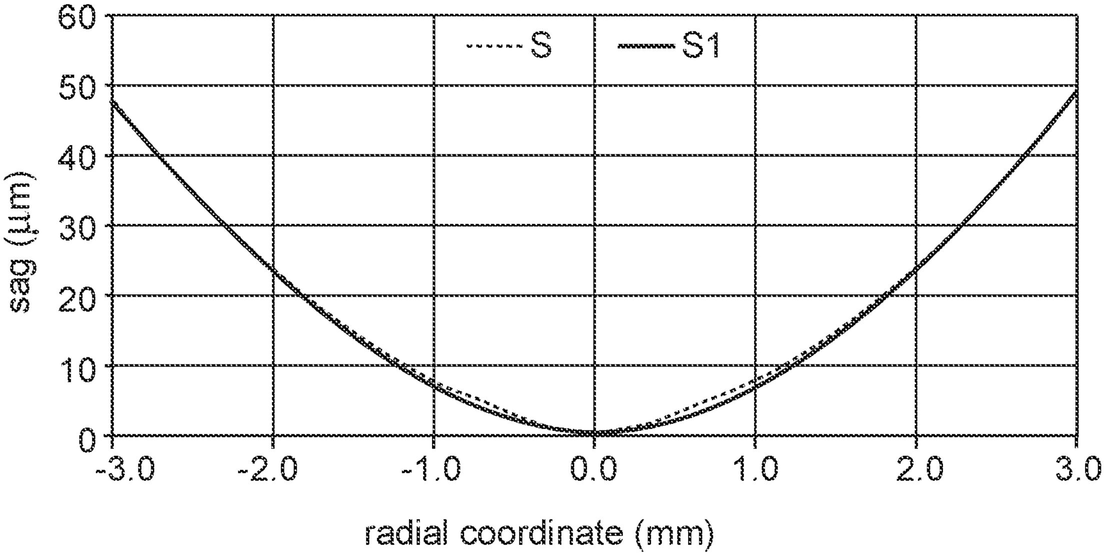
FIG. 10 shows schematically and exemplarily a sag function of a lens profile and a sag function of a standard aspheric profile which are of a different type than the sag functions shown in FIG. 2.

FIG. 10 shows schematically and exemplarily a lens profile sag function and a corresponding standard aspheric profile sag function for a lens surface providing an optical power of 6 diopter, i.e. an optical power which is smaller than the one provided by the lens surface 2 shown in FIG. 1 and representable by the sag function shown in FIG. 2. It can be seen in FIG. 10 that the deviations of the lens surface sag function providing such a smaller optical power from the corresponding standard aspheric profile sag function are higher than the corresponding deviations for the lens surface 2.

Figure 11:
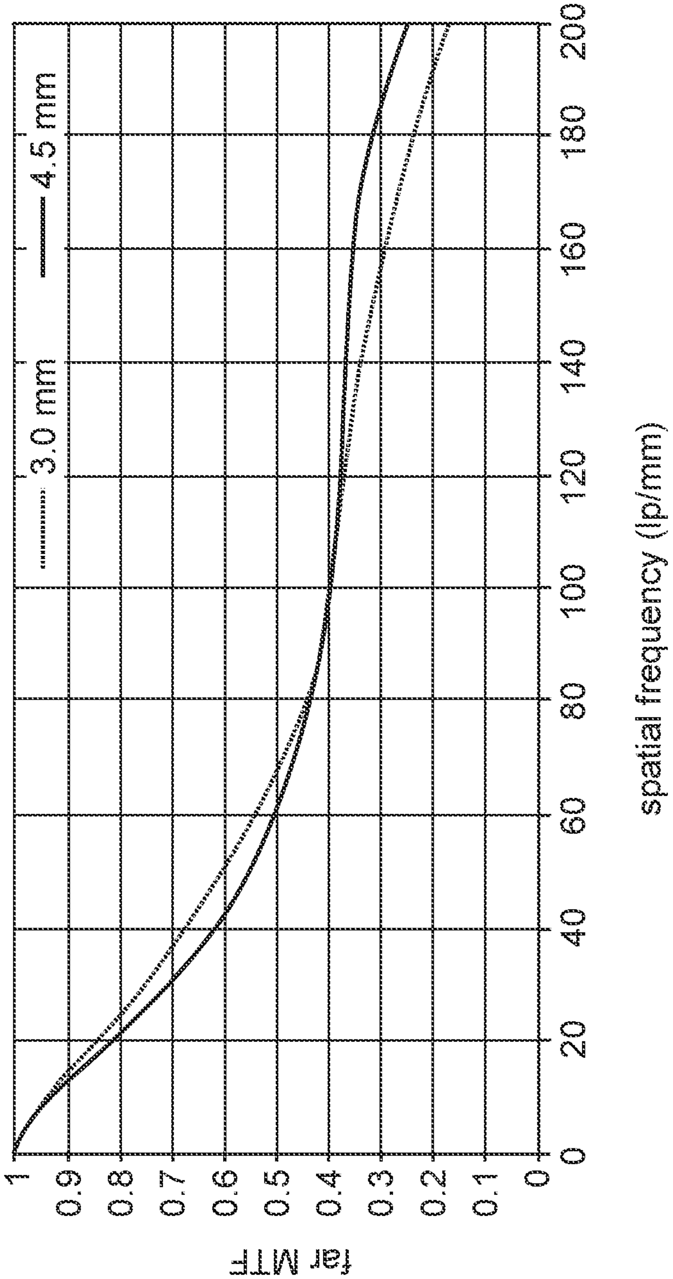
FIG. 11 shows schematically and exemplarily a far modulation transfer function of a different type than the one shown in FIG. 6.

In FIG. 11, a modulation transfer function calculated for far vision distances and with an aperture of 3.0 mm and 4.5 mm, respectively, is shown schematically and exemplarily for a lens having a lens surface as illustrated by FIG. 10 that has been placed in a human eye. From FIG. 11 it can be seen that, also for lens surfaces like the one illustrated by FIG. 10, the modulation transfer function falls off only relatively slowly towards higher spatial frequencies irrespective of the aperture.

Figure 12:
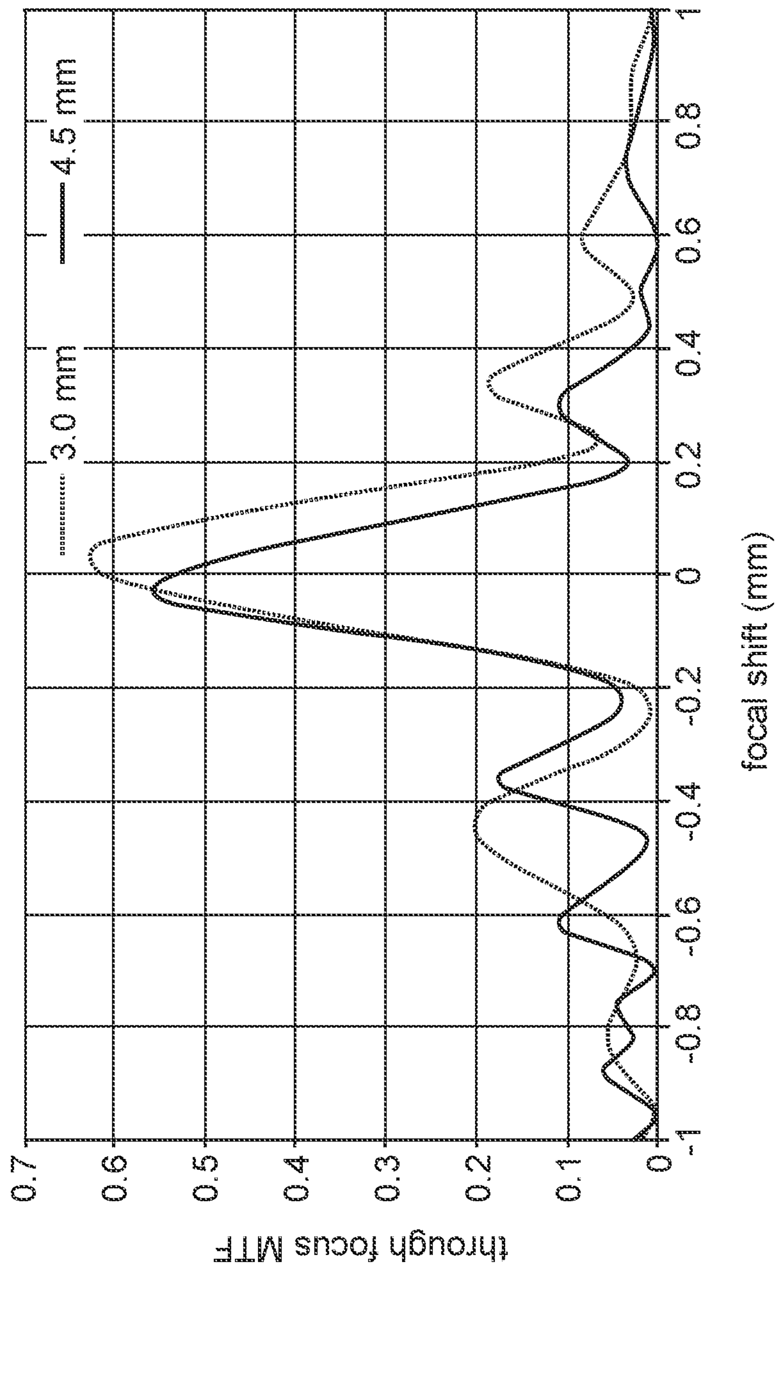
FIG. 12 shows schematically and exemplarily a through-focus modulation transfer function of a different type than the one shown in FIG. 7.

FIG. 12 shows schematically and exemplarily a through-focus modulation transfer function calculated for a human eye into which the lens whose surface is illustrated in FIG. 10 has been placed, at a spatial frequency of 50 line pairs per millimeter. The through-focus modulation transfer function is shown for an aperture of 3.0 mm and for an aperture of 4.5 mm. The horizontal axis indicates a focal shift, i.e. a focal distance measured relative to the focal distance corresponding to the reference optical power of the lens, wherein negative focal shifts correspond to higher optical powers with respect to the reference optical power. For both aperture sizes shown in FIG. 12, the width of the main, far-focus peak is widened with respect to a corresponding standard aspheric lens, particularly in the negative focal shift direction. Thus, FIG. 12 illustrates that the visual acuity of the human eye can be improved at intermediate vision distances also with a lens having a surface as illustrated in FIG. 10.

Figure 13:
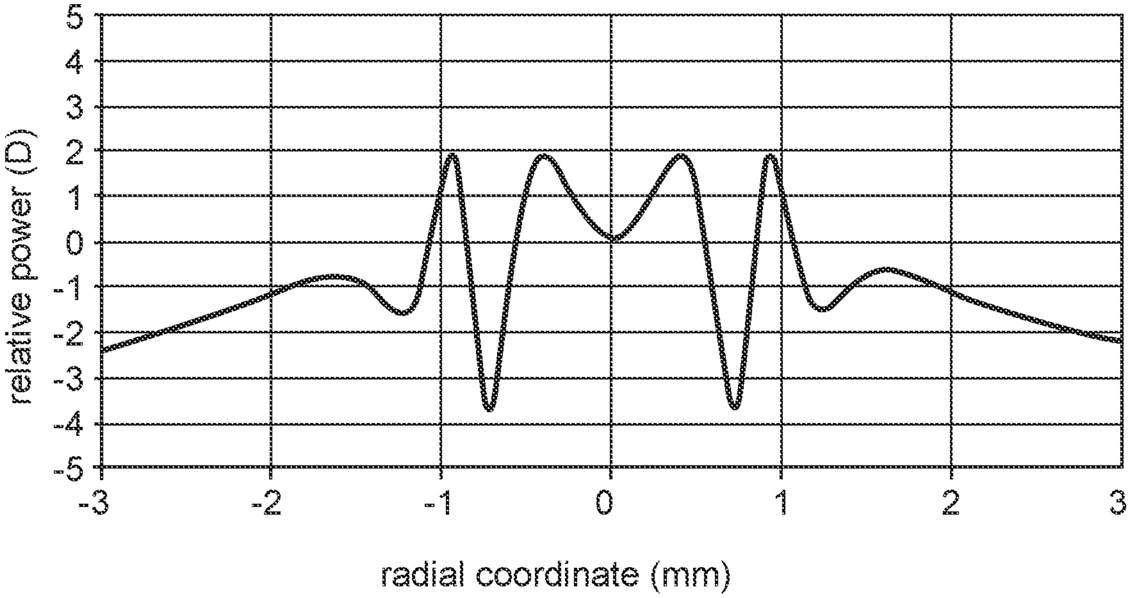
FIG. 13 shows schematically and exemplarily an optical power profile of an ophthalmic lens surface.

FIG. 13 shows schematically and exemplarily an optical power profile corresponding to a lens profile that is representable by a combination of the standard aspheric profile and an even-order aspheric profile. The shown power profile, which refers to an optical power measured relative to a reference optical power at the lens center, comprises local extrema corresponding to extremal points of the second-order derivative of a function representing the corresponding lens profile, i.e., for instance, the corresponding sag function of the lens. Towards an outer boundary of the lens surface, the optical power tends to a constant value. The optical power profile shown in FIG. 13 illustrates the relative spherical power and corresponds to the lens profile illustrated by FIGS. 2 to 5.

Figure 14:
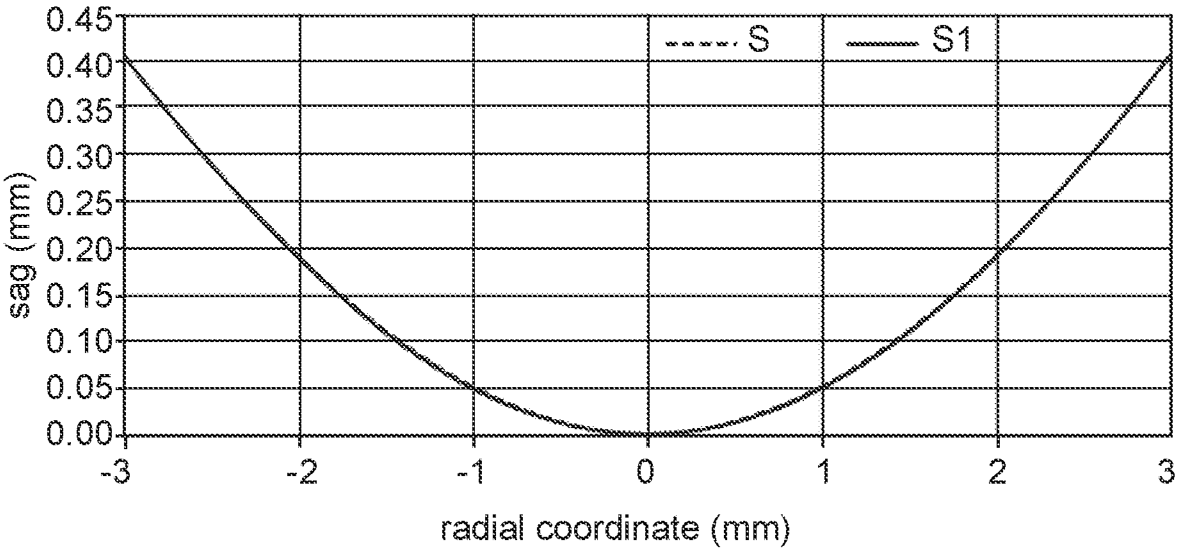
FIG. 14 shows schematically and exemplarily a sag function of a lens profile and a sag function of a standard aspheric profile of a further embodiment.
Figure 15:
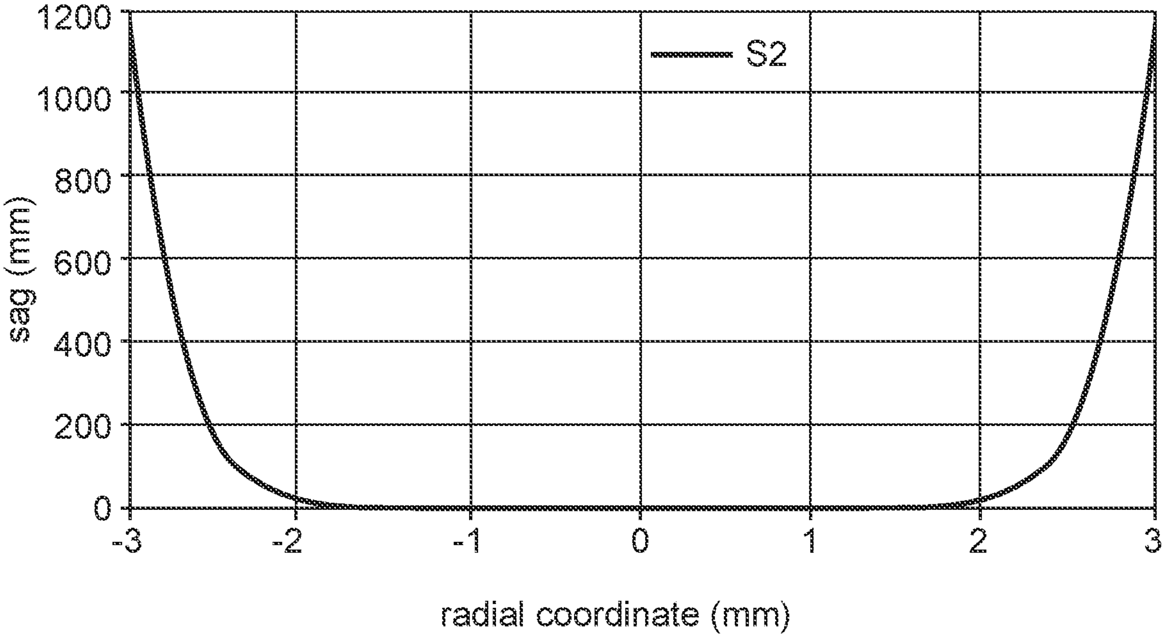
FIG. 15 shows schematically and exemplarily a sag function of an even-order aspheric profile of the further embodiment.

FIG. 14 shows schematically and exemplarily a graph of a further embodiment of the sag function S(r) which might represent the lens profile of the lens surface 2. Also FIG. 14, like FIG. 2, further shows schematically and exemplarily a graph of the sag function $S_1(r)$ of a standard aspheric profile, and FIG. 15 shows schematically and exemplarily a graph of the sag function $S_2(r)$ of an even-order aspheric profile corresponding to the further embodiment, wherein the lens profile whose sag function S(r) is shown in FIG. 14 may be represented by a combination of the standard aspheric profile whose sag function $S_1(r)$ is shown in FIG. 14 and the even-order aspheric profile whose sag function $S_2(r)$ is shown in FIG. 15. The combination of the two aspheric profiles, which corresponds to a combination of the respective sag functions $S_1(r)$ and $S_2(r)$, can be represented by a combination function M(r). The horizontal axes of the graphs shown in FIGS. 14 and 15 indicate a radial coordinate, i.e. a coordinate defining the radial distance r of the respective position on the lens surface 2 to the vertex, as measured perpendicularly to the central axis of the lens 1.

As can be seen in FIG. 14, the lens surface sag function S(r) is a smooth function of the radial position r, meaning that particularly the first derivative of S(r) is continuous in the whole range of radial positions. The function S(r) takes positive values ranging from 0 at the lens center r=0 to about 0.40 mm at an outer boundary of the lens surface at a radius $r_B$=3 mm. At the vertex, which is located at the lens center r=0, the lens surface sag function S(r) has a vanishing first order derivative. In fact, in FIG. 14, the difference between the lens surface sag function S(r) and the standard aspheric profile sag function $S_1(r)$ is hardly visible due to the resolution of the axes of the illustrated graph. The standard aspheric profile sag function $S_1(r)$ is defined by above equation (1), wherein the curvature c at the vertex of the lens surface corresponds to a convex shape and the conic constant k is negative, which means that the shown standard aspheric profile is parabolic. Also in this embodiment the value of c may be regarded as a reference curvature corresponding to a reference optical power of the lens 1, wherein the reference optical power might be selected based on a prescription in a clinical context. Moreover, also in this embodiment the standard aspheric profile may also be regarded as a standard monofocal profile, because the lens having a surface with such a standard aspheric profile would give rise to essentially a single, substantially localized focal point. The reference optical power of the lens 1 whose sag function S(r) is shown in FIG. 14 can be relatively high, and the conic constant k can be chosen appropriately. In particular, the conic constant k can −6 in this embodiment. The reference optical power corresponds to the value c of the curvature at the vertex of the lens surface 2.

The even-order aspheric profile sag function $S_2(r)$ shown in the graph of FIG. 15 is defined by above equation (2), wherein the horizontal axis of the shown graph indicates the radial coordinate whose absolute value corresponds to the radial distance r to the vertex of the lens surface 2, and the constants $A_{2n}$ are appropriately chosen. In particular, in this embodiment the following constants apply: $A_2=1.2\times10^{-3}$ $mm^{-1}$, $A^4=1.3\times10^{-2}$ $mm^{-3}$, $A_6=-6.0\times10^{-3}$ $mm^{-5}$, $A_8=1.8\times10^{-2}$ $mm^{-7}$, $A_{10}=2.2\times10^{-2}$ $mm^{-9}$; $A_{12}=0$, $A_{14}=0$, $A_{16}=0$.

Due to the very different resolution of the vertical axis of the graph illustrated in FIG. 15 as compared to the graph illustrated in FIG. 14, also in these figures it appears as if the even-order aspheric profile sag function $S_2(r)$ is substantially 0 over half the radial extent of the lens surface 2. However, already in this inner region of the lens surface 2, the even-order aspheric profile is not negligible with respect to the standard aspheric profile whose sag function $S_1(r)$ is shown in FIG. 14.

Figure 16:
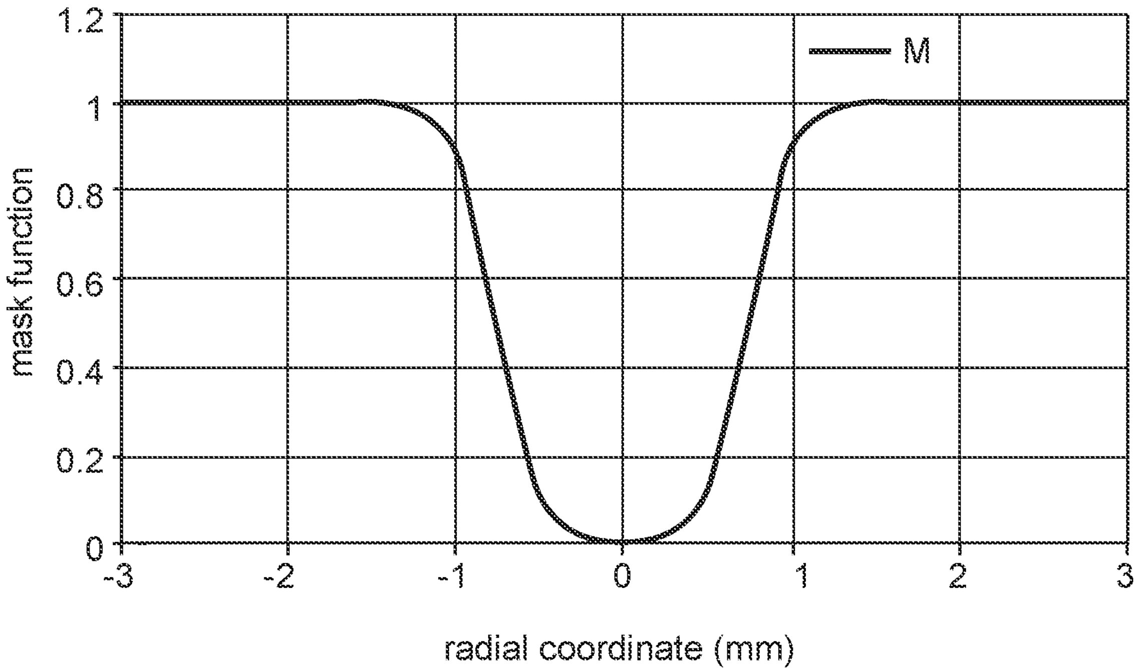
FIG. 16 shows schematically and exemplarily a combination function of the further embodiment.

A further embodiment of the combination function M(r) corresponding to the exemplary lens 1 is shown in FIG. 16. It is defined by a smooth function of the radial position r, and is of the form given in above equation (5), wherein the constants A and ρ are appropriately chosen. In particular, in this embodiment the constant A is 4.0 $mm^{-1}$, and the constant ρ is 0.74 mm.

The lens surface sag function for the lens surface 2 shown in FIG. 14 is a combination of the standard aspheric profile sag function $S_1(r)$ shown in FIG. 14 and the even-order aspheric profile sag function $S_2(r)$ shown in FIG. 15, wherein the combination of the two sag functions is defined by the combination function M(r) shown in FIG. 16. Also in this embodiment, the combination function M(r) depends on the radial distance to the vertex such that the contribution of the standard aspheric profile sag function $S_1(r)$ and the contribution of the even-order aspheric profile sag function $S_2(r)$ to the lens profile sag function S(r) of the lens 1 at a certain radial distance to the vertex depends on the radial distance r. The combination function M(r) may therefore also be regarded as a mask function masking the contributions from the two different aspheric profiles, wherein the degree of masking depends on the radial position r.

Also in this embodiment, the lens surface 2 described by the resulting lens profile sag function S(r) is shaped such that, in a region immediately surrounding the vertex of the lens surface 2, the lens profile converges to the sum of the standard aspheric profile, described by $S_1(r)$, and the even-order aspheric profile, described by $S_2(r)$, with decreasing radial distance r to the vertex and, in an outer region surrounding the vertex, the lens profile converges to the standard aspheric profile with increasing radial distance r to the vertex. Moreover, also in this embodiment, since the standard aspheric profile sag function $S_1(r)$, the even-order aspheric profile sag function $S_2(r)$ and the combination function M(r) are all smooth functions in this embodiment, also the combined sag function, i.e. the lens profile sag function S(r), is smooth.

Figure 17:
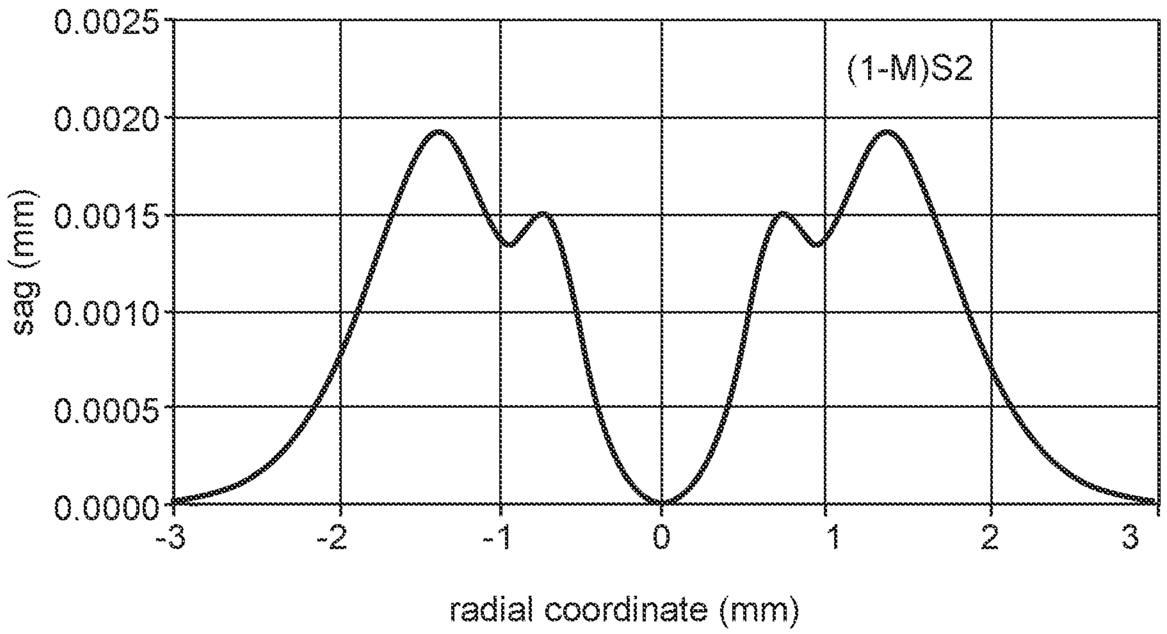
FIG. 17 shows schematically and exemplarily the difference between the sag function of the lens profile and the sag function of the standard aspheric profile of the further embodiment.

The second term of equation (4), which corresponds to the difference $(1-M(r))\,S_2(r)$ between the lens profile sag function S(r) and the standard aspheric profile sag function $S_1(r)$, is shown in FIG. 17 for the embodiment illustrated in FIGS. 14 to 16. From the values of this difference function $(1-M(r))\,S_2(r)$ as seen on the vertical axis of the graph illustrated in FIG. 17, it is apparent why the difference between the lens profile sag function S(r) and the standard aspheric profile sag function $S_1(r)$ is hardly visible in FIG. 14.

As will be illustrated in the following, while the values assumed by the difference function $(1-M(r))\,S_2(r)$ shown in FIG. 17 seem to be small, corresponding to only a seemingly small deviation of the lens surface 2 from a standard aspheric surface, also in this embodiment the optical effects generated by the seemingly small deviation are surprisingly large.

Figure 18:
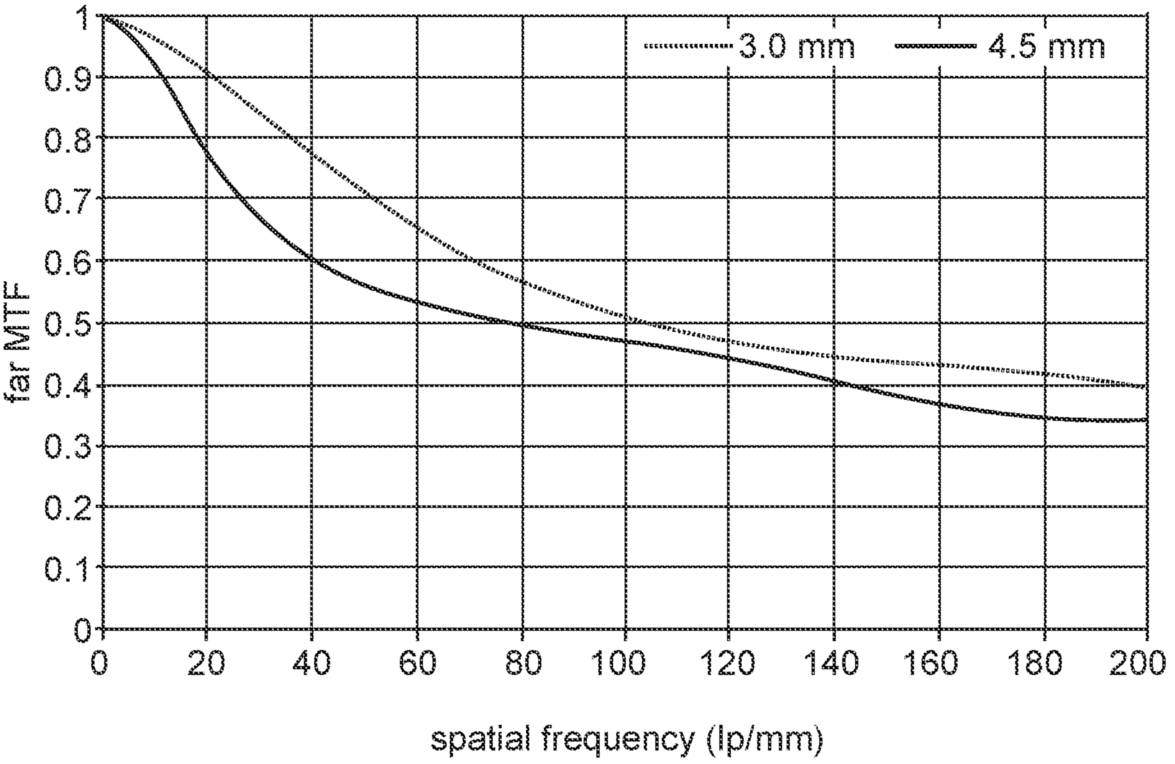
FIG. 18 shows schematically and exemplarily a far modulation transfer function for the further embodiment.

FIG. 18 shows schematically and exemplarily an MTF calculated for a human eye into which the ophthalmic lens 1 has been placed, with an aperture of 3.0 mm and 4.5 mm, respectively, wherein the calculation was performed for far visual distances. It can be seen in FIG. 18 that the modulation transfer function, which may be regarded as a measure of imaging quality, falls off only relatively slowly towards higher spatial frequencies irrespective of the aperture.

Figure 19:
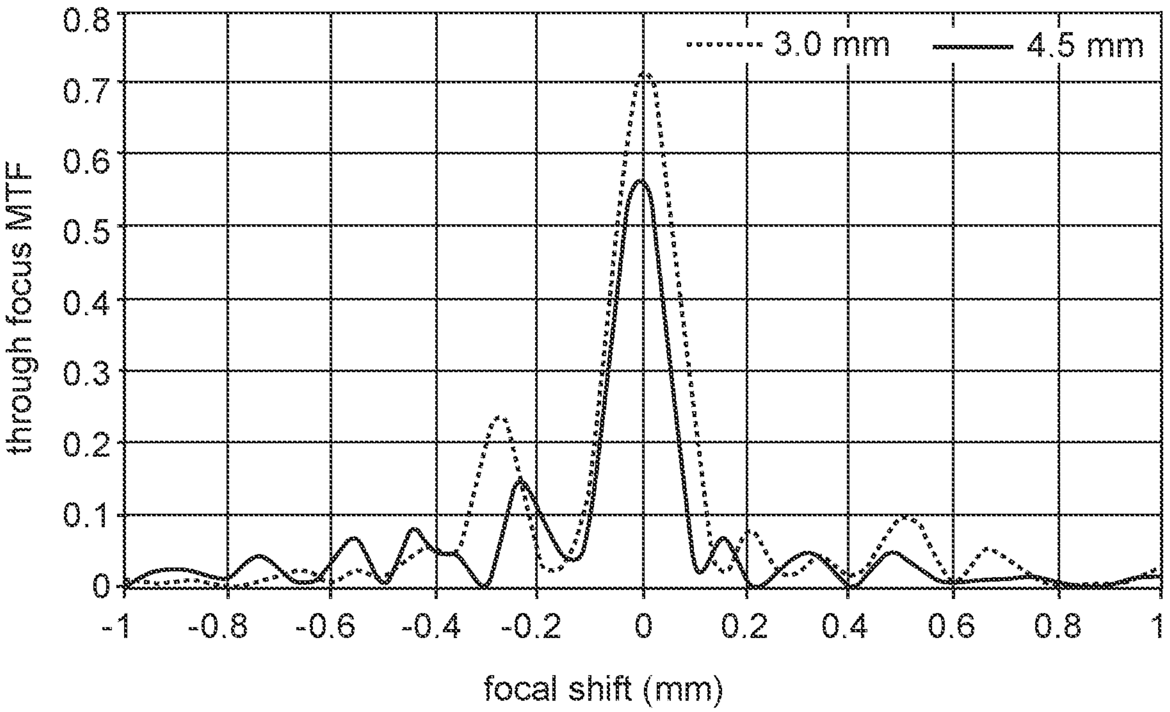
FIG. 19 shows schematically and exemplarily a through-focus modulation transfer function for the further embodiment.

FIG. 19 shows schematically and exemplarily a through-focus modulation transfer function calculated for a human eye into which the lens 1 with the lens profile of the further embodiment illustrated in FIGS. 14 to 17 has been placed, at a spatial frequency of 50 line pairs per millimeter. In FIG. 19, the through-focus modulation transfer function is shown for an aperture of 3.0 mm and for an aperture of 4.5 mm. The horizontal axis indicates a focal shift, i.e. a focal distance measured relative to the focal distance corresponding to the reference optical power of the lens 1, wherein negative focal shifts correspond to higher optical powers with respect to the reference optical power. For both aperture sizes shown in FIG. 19, the width of the main, far-focus peak is widened with respect to a corresponding standard aspheric lens, particularly in the negative focal shift direction. Thus, FIG. 19 illustrates that the visual acuity of the human eye can be improved at intermediate vision distances.

Figure 20:
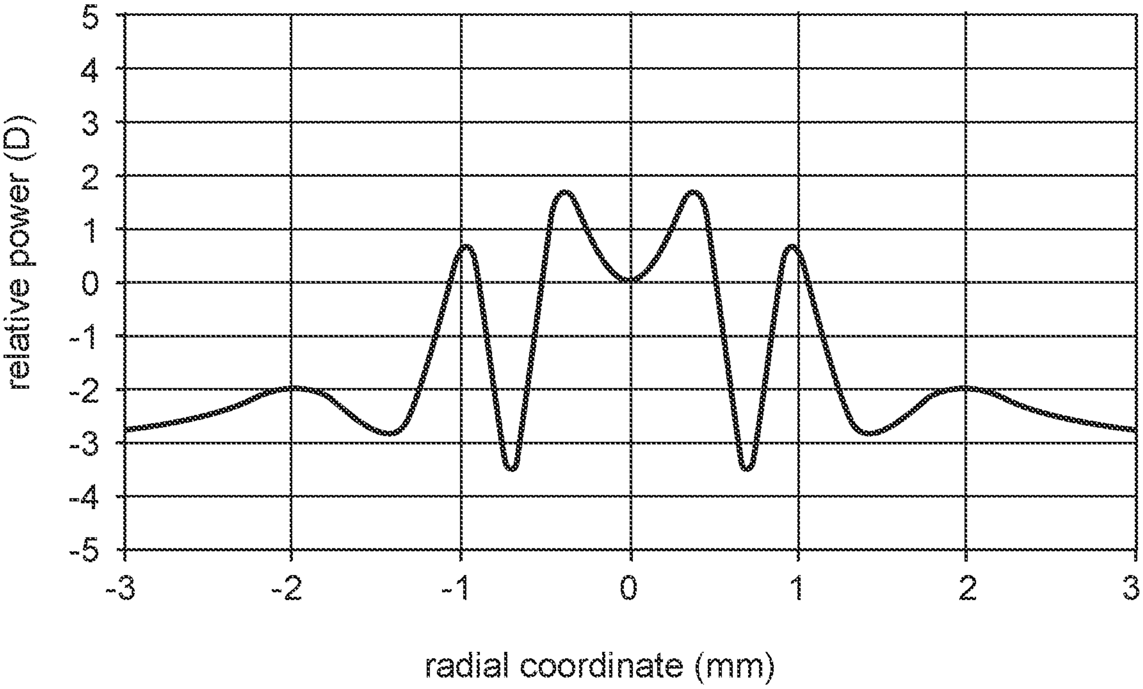
FIG. 20 shows schematically and exemplarily an optical power profile of the ophthalmic lens surface of the further embodiment.

FIG. 20 shows schematically and exemplarily an optical power profile corresponding to a lens profile that is representable by a combination of the standard aspheric profile and an even-order aspheric profile. The shown power profile, which refers to an optical power measured relative to a reference optical power at the lens center, comprises local extrema corresponding to extremal points of the second-order derivative of a function representing the corresponding lens profile, i.e., for instance, the corresponding sag function of the lens. Towards an outer boundary of the lens surface, the optical power tends to a constant value. The optical power profile shown in FIG. 20 illustrates the relative spherical power and corresponds to the lens profile illustrated by FIGS. 14 to 17.

Figure 21:
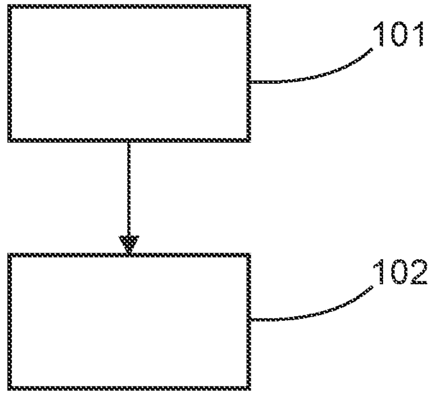
FIG. 21 shows a flowchart exemplarily illustrating an embodiment of a manufacturing method for manufacturing an ophthalmic lens.

In the following, an embodiment of a manufacturing method for manufacturing an ophthalmic lens will exemplarily be described with reference to a flowchart shown in FIG. 21.

In step 101 a mathematical combination of a standard aspheric profile and an even-order aspheric profile is provided, wherein the aspheric profiles are combined such that, in a region immediately surrounding the vertex of a lens surface, the lens profile converges to a sum of the standard aspheric profile and the even-order aspheric profile with decreasing radial distance to the vertex and, in an outer region surrounding the vertex, the lens profile converges to the standard aspheric profile with increasing radial distance to the vertex.

In step 102 the ophthalmic lens is formed such that a surface of the lens is in accordance with the provided combination of the standard aspheric profile and the even-order aspheric profile. The lens might be formed, for instance, by using a known molding procedure and a known lathe cutting procedure, or by another technique generally used for manufacturing lenses.

Although in above described embodiments, the lenses are rotationally symmetric, the lenses could also have lens surfaces with a toric shape. In that case, a first lens profile could be provided in a first radial direction of the lens surface and a second lens profile could be provided for a second radial direction of the lens surface, wherein the first and the second radial direction may be perpendicular to each other.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

Any reference signs in the claims should not be construed as limiting the scope.

The invention claimed is:

1. An ophthalmic lens comprising a lens surface with a lens profile being representable by a combination of a standard aspheric profile and an even-order aspheric profile, wherein the aspheric profiles are combined such that, in a region immediately surrounding the vertex of the lens surface, the lens profile converges to a sum of the standard aspheric profile and the even-order aspheric profile with decreasing radial distance to the vertex and, in an outer region surrounding the vertex, the lens profile converges to the standard aspheric profile with increasing radial distance to the vertex, wherein a sag function of the lens profile is defined by the equation $$S(r)=M(r)S_1(r)+(1-M(r))(S_1(r)+S_2(r)),$$

wherein r denotes the radial distance to the vertex of the lens surface, $S_1(r)$ denotes a sag function of the standard aspheric profile, $S_2(r)$ denotes a sag function of the even-order aspheric profile and M(r) denotes a combination function, wherein the sag function of the standard aspheric profile is defined by the equation $$S_1(r)=\frac{cr^2}{1+\sqrt{1-(1+k)c^2r^2}},$$

wherein r denotes the radial distance to the vertex of the lens surface, c denotes the curvature at the vertex of the lens surface and k denotes the conic constant, wherein the sag function of the even-order aspheric profile is defined by the equation $$S_2(r) = \sum_{n=1}^{8} A_{2n} r^{2n},$$

wherein r denotes the radial distance to the vertex of the ophthalmic lens surface and the $A_{2n}$ are constants, wherein the combination function is defined by $$M(r)=\tfrac{1}{2}(1+\tanh(A(r-\rho))),$$

wherein A and ρ are constants.

2. The ophthalmic lens as defined by claim 1, wherein the combination of the standard aspheric profile and the even-order aspheric profile is representable by a smooth function of the radial position.

3. The ophthalmic lens as defined by claim 2, wherein the combination of the standard aspheric profile and the even-order aspheric profile is representable by a function of the radial position, which has a first-order derivative of zero at the vertex of the lens surface.

4. The ophthalmic lens as defined by claim 1, wherein the combination of the standard aspheric profile and the even-order aspheric profile is representable by a function of the radial position, which has a first-order derivative of zero at the vertex of the lens surface.

5. The ophthalmic lens as defined by claim 1, wherein the combination of the standard aspheric profile and the even-order aspheric profile is representable by a function of the radial position, which changes the sign of the second-order derivative with increasing radial position.

6. The ophthalmic lens as defined by claim 1, wherein the curvature c at the vertex of the lens surface is a) larger than or equal to 0.005 $mm^{-1}$ and b) smaller than or equal to 0.25 $mm^{-1}$.

7. The ophthalmic lens as defined by claim 6, wherein the conic constant k is a) larger than or equal to −800 and b) smaller than or equal to 5.

8. The ophthalmic lens as defined by claim 1, wherein the conic constant k is a) larger than or equal to −800 and b) smaller than or equal to 5.

9. The ophthalmic lens as defined by claim 1, wherein the constant A is larger than 2.0 $mm^{-1}$ and smaller than 10.0 $mm^{-1}$, and the constant ρ is larger than 0.3 mm and smaller than 2.5 mm.

10. The ophthalmic lens as defined by claim 1, wherein the ophthalmic lens is an intraocular lens.

11. A manufacturing method for manufacturing the ophthalmic lens as defined by claim 1, wherein the manufacturing method comprises forming a lens profile of the lens surface of the ophthalmic lens.

* * * * *